United States Patent [19]

Kohn et al.

[11] 4,332,792

[45] Jun. 1, 1982

[54] INSECT ATTRACTANT

[75] Inventors: Gustave K. Kohn, Palo Alto; Richard L. Baughn, San Francisco, both of Calif.

[73] Assignee: Zoecon Corporation, Palo Alto, Calif.

[21] Appl. No.: 168,862

[22] Filed: Jul. 14, 1980

[51] Int. Cl.³ ............................................. A01N 25/00
[52] U.S. Cl. ...................................... 424/84; 424/361
[58] Field of Search .................... 424/84, 77, 17, 361; 43/114, 135; 260/106

[56] References Cited

U.S. PATENT DOCUMENTS 3,325,355  6/1967  Goodhue .............................. 424/84

FOREIGN PATENT DOCUMENTS 46-28800  8/1971  Japan ..................................... 424/266
901693  7/1962  United Kingdom ................... 424/84
925567  5/1963  United Kingdom ................ 424/266

OTHER PUBLICATIONS

Materials Tested as Insect Attractants by Beroza et al., Agriculture Handbook No. 239, USDA, Jun. 1963, pp. 82, 110 & 117.
J. of Food Science, vol. 39 (1974), pp. 1216 & 1217.
Chemical Abstracts, vol. 68, item 38187h (1968).
Henry, The Plant Alkaloids, 2nd Ed. (1924), pp. 21–23 and 4th Ed. (1949), pp. 7 & 8, published by The Blakiston Co., Phila., Pa.

*Primary Examiner*—Donald B. Moyer
*Attorney, Agent, or Firm*—Donald W. Erickson; Jacqueline S. Larson; Thomas T. Gordon

[57] ABSTRACT

Preparation of an insect attractant comprising the pyrolyzate of N-methylnicotinic acid and starch syrup for the control of insects such as cockroaches.

10 Claims, No Drawings

INSECT ATTRACTANT

This invention relates to a novel composition of matter which is useful for the control of insects. More particularly, the present invention relates to a novel composition which is particularly attractant for cockroaches.

Insects may be controlled through mechanisms such as contact with an insecticide as by spraying, ingestion of food containing an insecticide, or trapping using an adhesive to hold the insect or other means. The insect control mechanism used depends on factors such as the natural habits of the insect and the environment. Insects such as the cockroach tend to harbor in very inaccessible areas making contact with insecticide difficult. While fumigation with insecticide will oftentimes overcome accessability difficulties, the cockroach is frequently a pest in environments where it is undesirable to use fumigation such as the home and restaurants. The composition of the present invention is particularly useful in controlling insects that harbor in inaccessable areas in the home, restaurants, hotels, and the like where the effective application of insecticide is difficult. The composition of the present invention is useful as an attractant in conjunction with traps which may be placed near the harboring sites of the insects. The attractant of the present invention can be mixed with an insecticide and carrier to prepare a bait which may be placed at strategic spots of the insect infestation.

The attractant of the present invention is prepared by the pyrolysis of a mixture comprising N-methylnicotinic acid and starch syrup. The amount of N-methylnicotinic acid in the mixture can range from about 0.1 to 50 percent, by weight. Usually, the amount of N-methylnicotinic acid is about 1 to 30 percent of the mixture. In the preferred embodiment, the mixture contains from about 5 to 15 percent of N-methylnicotinic acid. The attractant is prepared, in accordance with the present invention, by preparing a mixture comprising N-methylnicotinic acid and starch syrup and then heating the mixture to obtain the pyrolyzate. As a guide, the pyrolyzate can be prepared by heating the mixture at about 100° to 250° C. for about 5 minutes to 120 minutes. The mixture is heated for a shorter period of time according to the use of increased temperature. For example, a heating time of about 60 minutes at a temperature of about 190°-200° C. provides a pyrolyzate in accordance with the present invention. The pyrolyzate can be used in dry, granular form or diluted with a liquid or solid carrier such as water, silicon, or the like.

The starch syrup component of the mixture for preparing the attractant of the present invention is a concentrated water solution of partial hydrolyzates of starch. Starch syrups suitable in the practice of the present invention are described by KirkOthmer, Encyclopedia of Chemical Technology, 2nd Edition, Vol. 6, pp. 926-930 (1965). The term "starch syrup", as used herein and the appended claims, means starch syrups, such as corn syrup, and hydrolyzates thereof including simple hexoses. In the preparation of an attractant according to the present invention, the ratio of N-methylnicotinic acid to starch syrup, in the mixture to be pyrolyzed, is computed based on the solids content of the syrup. In preparing the pyrolysis product, it does not appear to be important that the water of the starch syrup be removed. In lieu of liquid starch syrup in the practice of the invention, there can be used the dry form referred to as starch syrups solids.

The pyrozylate of a mixture comprising N-methylnicotinic acid and starch syrup can be used as the attractant in insect traps such as described in U.S. Pat. Nos. 3,851,417, 3,940,874 and 4,112,609 or as a component in a bait in the manner described in U.S. Pat. Nos. 4,049,460 and 4,160,824.

The following examples are provided to illustrate the practice of the present invention.

EXAMPLE 1

Light Karo corn syrup (600 mg) and N-methylnicotinic acid (60 mg) were placed into a 3-dram glass vial capped with a plastic stopper. A small hole was made in the cap to prevent pressure build-up during heating. The mixture was heated at 190°-200° C. in an oil bath for one hour to pyrolyze the material.

Karo is the brand name of Best Foods Corporation.

EXAMPLE 2

D(+)-glucose (600 mg), N-methylnicotinic acid (60 mg), and water (0.5 ml.) were placed in a screw-capped 3-dram vial. The sealed vial was heated in a small metal bomb for one hour at about 200° C. to pyrolyze the mixture.

The pyrolyzate of Example 1 was tested by placing a small amount in a paper cockroach trap (trap I). The test included the same type of traps containing an equal amount of Light Karo syrup alone and N-methylnicotinic acid plus Light Karo syrup (not pyrolyzed)-Traps II and III, respectively. The amount of test substance in each trap was about 50 mg. The traps were placed in a room with German cockroaches *Blattella germanica* (Linnaeus) and placement rotated every 8 hours. The average catch per trap was I-38.5, II-12; and III-13.

To the pyrolyzate solution of Example 2 was added 2 ml of water, 10 ml of corn oil and 3 drops of Tween 20. One ml of the thus-prepared solution was placed on each of four cotton dental wicks. Each treated wick was placed in the center of a trap. The traps were placed at random in a room measuring about 8'×16'. Four traps containing no wick were placed in the same room, at random, as controls. The traps were left in the room about 18 hours of which 12 hours were without light. The traps with the treated wicks contained an average count of 60 German roaches. The control contained an average count of 14.

What is claimed is:

1. A process for the manufacture of an insect attractant which comprises pyrolyzing a mixture comprising N-methylnicotinic acid and starch syrup, said mixture containing from about 0.1 to 50 percent, by weight, of said N-methylnicotinic acid, and said pyrolyzing being conducted by heating said mixture at about 100° to 250° C. for about 5 minutes to 120 minutes.

2. The process according to claim 1 wherein the mixture contains from about 1 to 30 percent of said acid.

3. The process according to claim 1 wherein the mixture contains from about 5 to 15 percent of said acid.

4. The insect attractant pyrolyzate prepared according to claim 1.

5. The pyrolyzate of claim 4 wherein the mixture contains from about 1 to 30 percent of said acid.

6. The pyrolyzate of claim 5 wherein the mixture contains from about 5 to 15 percent of said acid.

7. In a method for the control of insects using an attractant, the improvement which comprises using the pyrolyzate prepared according to claim 1 as the attractant.

8. The method of claim 7 wherein the insect is a cockroach.

9. The method of claim 8 wherein the mixture contains from about 1 to 30 percent of said acid.

10. The method of claim 8 wherein the mixture contains from about 5 to 15 percent of said acid.

* * * * *